US006986744B1

(12) United States Patent
Krivitski

(10) Patent No.: US 6,986,744 B1
(45) Date of Patent: Jan. 17, 2006

(54) METHOD AND APPARATUS FOR DETERMINING BLOOD FLOW DURING A VASCULAR CORRECTIVE PROCEDURE

(75) Inventor: Nikolai M. Krivitski, Ithaca, NY (US)

(73) Assignee: Transonic Systems, Inc., Ithaca, NY (US)

( * ) Notice: Subject to any disclaimer, the term of this patent is extended or adjusted under 35 U.S.C. 154(b) by 0 days.

(21) Appl. No.: 09/241,455

(22) Filed: Feb. 2, 1999

(51) Int. Cl.
  *A61B 5/02* (2006.01)

(52) U.S. Cl. .................................................. 600/504
(58) Field of Classification Search ............... 600/504, 600/505, 481, 466, 467, 468, 469, 470, 526; 604/246
See application file for complete search history.

(56) References Cited

U.S. PATENT DOCUMENTS

| | | |
|---|---|---|
| 3,268,728 A | 8/1966 | Stoddart et al. |
| 3,347,224 A | 10/1967 | Adams |
| 3,516,399 A | 6/1970 | Barefoot |
| 3,604,263 A | 9/1971 | Neuilly et al. |
| 3,651,318 A | 3/1972 | Czekejewski |
| 3,677,648 A | 7/1972 | Dorsch |
| 3,757,773 A | 9/1973 | Kolin |
| 3,789,831 A | 2/1974 | Kopaniky et al. |
| 3,835,839 A | 9/1974 | Brown |
| 3,835,840 A | 9/1974 | Mount |
| 3,896,373 A | 7/1975 | Zelby |
| 3,920,004 A | 11/1975 | Nakayama |
| 3,994,284 A | 11/1976 | Voelker |
| 3,996,924 A | 12/1976 | Wheeler |
| 3,996,925 A | 12/1976 | Djordjevich |
| 4,205,688 A | 6/1980 | Hauser et al. |
| 4,212,298 A | 7/1980 | Gezari |
| 4,217,910 A | 8/1980 | Khalil |
| 4,296,754 A | 10/1981 | Hennig et al. |
| 4,314,563 A | 2/1982 | Wheeler |
| 4,418,700 A | 12/1983 | Warner |
| 4,450,527 A | 5/1984 | Sramek |

(Continued)

FOREIGN PATENT DOCUMENTS

| | | |
|---|---|---|
| WO | WO 85/00510 | 2/1985 |
| WO | WO 94/05208 | 3/1994 |

OTHER PUBLICATIONS

Fresenius Medical Care, Contact Home Search Overview, Jan. 1, 1999, heep://www.fmc–ag.de/daily/kidintro.htm.
Angioplasty Links Page, Oct. 5, 1998.
Heart Information Network, Heartinfo.org, Oct. 5, 1998.
Jerry Goldstone, MD; K. Wayne Johnston, MD; Erick C. Martin, MD; Ernest J. Ring, MD; James B Spies, MD, Members; Guidelines for peripheral Percutaneous Transluminal Angiopasty of the Abdominal Aorta and Lower Extremity Vessels.
Brijesh Bhambi, MD, FACC, FACA, Central Cardiology Medical Clinic; Invasive Cardiology Procedures; Oct. 5, 1998.
Mayo Clinic Coronary Angioplasty; Using Balloons to Open Clogged Heart Arteries; Oct. 5, 1998.

*Primary Examiner*—Max F. Hindenburg
*Assistant Examiner*—Brian Szmal
(74) *Attorney, Agent, or Firm*—Brian B. Shaw, Esq.; Stephen B. Salai, Esq.; Harter, Secrest & Emery

(57) ABSTRACT

A method and apparatus for determining an angioplasty induced blood flow changes, wherein the apparatus includes the catheter having a port for introducing a blood property change in a downstream sensor. The downstream sensor and the catheter are configured to space the sensor from an adjacent vessel wall so as to minimize effects of the vessel wall during sensing of the blood property change.

13 Claims, 4 Drawing Sheets

U.S. PATENT DOCUMENTS

| | | | | |
|---|---|---|---|---|
| 4,484,582 A | | 11/1984 | Rottenberg et al. | |
| 4,502,488 A | * | 3/1985 | Degironimo et al. | 600/505 |
| 4,541,433 A | | 9/1985 | Baudino | |
| 4,542,748 A | | 9/1985 | Roy | |
| 4,572,206 A | | 2/1986 | Geddes et al. | |
| 4,587,975 A | | 5/1986 | Salo et al. | |
| 4,595,015 A | | 6/1986 | Jansen et al. | |
| 4,610,258 A | | 9/1986 | Colsher | |
| 4,621,646 A | | 11/1986 | Bryant | |
| 4,632,125 A | | 12/1986 | Webler et al. | |
| 4,674,518 A | | 6/1987 | Salo | |
| 4,676,253 A | | 6/1987 | Newman et al. | |
| 4,685,470 A | | 8/1987 | Sekii et al. | |
| 4,730,623 A | | 3/1988 | Lee | |
| 4,739,771 A | | 4/1988 | Manwaring | |
| 4,785,823 A | | 11/1988 | Eggers et al. | |
| 4,802,489 A | | 2/1989 | Nitzan | |
| 4,811,741 A | | 3/1989 | Shell et al. | |
| 4,817,624 A | | 4/1989 | Newbower | |
| 4,836,214 A | | 6/1989 | Sramek | |
| 4,841,981 A | | 6/1989 | Tanabe et al. | |
| 4,852,580 A | | 8/1989 | Wood | |
| 4,941,475 A | | 7/1990 | Williams et al. | |
| 4,953,556 A | | 9/1990 | Evans | |
| 4,957,110 A | | 9/1990 | Vogel et al. | |
| 4,979,514 A | | 12/1990 | Sekii et al. | |
| 5,000,190 A | | 3/1991 | Petre | |
| 5,009,231 A | | 4/1991 | Schmitt et al. | |
| 5,009,234 A | | 4/1991 | Alt | |
| 5,014,715 A | | 5/1991 | Chapolini | |
| 5,046,503 A | * | 9/1991 | Schneiderman | |
| 5,058,583 A | | 10/1991 | Geddes et al. | |
| 5,080,106 A | | 1/1992 | Sekii et al. | |
| RE33,834 E | | 3/1992 | Warner | |
| 5,092,339 A | | 3/1992 | Geddes et al. | |
| 5,101,828 A | | 4/1992 | Welkowitz et al. | |
| 5,121,749 A | | 6/1992 | Nassi et al. | |
| 5,146,414 A | | 9/1992 | McKown et al. | |
| 5,174,299 A | | 12/1992 | Nelson | |
| 5,176,144 A | | 1/1993 | Yoshikoshi et al. | |
| 5,178,153 A | | 1/1993 | Einzig | |
| 5,183,051 A | | 2/1993 | Kraidin et al. | |
| 5,199,438 A | | 4/1993 | Pearlman | |
| 5,211,177 A | | 5/1993 | Chesney et al. | |
| 5,217,019 A | | 6/1993 | Hughes | |
| 5,241,965 A | | 9/1993 | Mick | |
| 5,241,966 A | | 9/1993 | Finkelstein et al. | |
| 5,271,408 A | | 12/1993 | Breyer et al. | |
| 5,277,191 A | | 1/1994 | Hughes | |
| 5,289,823 A | | 3/1994 | Eckerle | |
| 5,291,896 A | | 3/1994 | Fonger et al. | |
| 5,316,004 A | | 5/1994 | Chesney et al. | |
| 5,345,932 A | | 9/1994 | Yafuso et al. | |
| 5,346,508 A | | 9/1994 | Hastings | |
| 5,354,318 A | | 10/1994 | Taepke | |
| 5,363,853 A | | 11/1994 | Lieber et al. | |
| 5,363,856 A | | 11/1994 | Hughes et al. | |
| 5,373,850 A | | 12/1994 | Kohno et al. | |
| 5,383,468 A | | 1/1995 | Nakayama et al. | |
| 5,390,679 A | | 2/1995 | Martin | |
| 5,397,308 A | | 3/1995 | Ellis et al. | |
| 5,400,793 A | | 3/1995 | Wesseling | |
| 5,409,009 A | | 4/1995 | Olson | |
| RE34,938 E | | 5/1995 | Serikov et al. | |
| 5,423,322 A | | 6/1995 | Clark et al. | |
| 5,423,326 A | | 6/1995 | Wang et al. | |
| 5,439,003 A | | 8/1995 | Schnurer et al. | |
| 5,443,073 A | | 8/1995 | Wang et al. | |
| 5,474,080 A | | 12/1995 | Hughes | |
| 5,493,100 A | | 2/1996 | Renger | |
| 5,494,031 A | | 2/1996 | Hoeft | |
| 5,505,204 A | | 4/1996 | Picot et al. | |
| 5,509,424 A | | 4/1996 | Al-Ali | |
| 5,515,857 A | | 5/1996 | Tsujino et al. | |
| 5,520,190 A | | 5/1996 | Benedit et al. | |
| 5,566,677 A | | 10/1996 | Raines et al. | |
| 5,579,778 A | | 12/1996 | Baker et al. | |
| 5,595,181 A | | 1/1997 | Hubbard | |
| 5,595,182 A | | 1/1997 | Krivitski | |
| 5,598,841 A | | 2/1997 | Taniji et al. | |
| 5,617,870 A | | 4/1997 | Hastings et al. | |
| 5,636,638 A | | 6/1997 | Carlson et al. | |
| 5,682,899 A | | 11/1997 | Nashef et al. | |
| 5,685,989 A | | 11/1997 | Krivitski et al. | |
| 5,687,726 A | | 11/1997 | Hoeft | |
| 5,687,733 A | | 11/1997 | McKown | |
| 5,692,514 A | | 12/1997 | Bowman | |
| 5,697,371 A | | 12/1997 | Aoyagi et al. | |
| 5,706,808 A | | 1/1998 | Kleinerman | |
| 5,722,415 A | | 3/1998 | Rom et al. | |
| 5,722,997 A | | 3/1998 | Nedungadi et al. | |
| 5,724,982 A | | 3/1998 | Schnurer et al. | |
| 5,782,774 A | | 7/1998 | Scmulewitz | |
| 5,791,349 A | | 8/1998 | Shmulewitz | |
| 5,797,395 A | | 8/1998 | Martin | |
| 5,807,258 A | | 9/1998 | Cimochowski et al. | |
| 5,807,269 A | | 9/1998 | Quinn et al. | |
| 5,827,192 A | | 10/1998 | Gopakumaran et al. | |
| 5,830,365 A | | 11/1998 | Schneditz | |
| 6,036,654 A | * | 3/2000 | Quinn et al. | 600/504 |
| 6,053,913 A | * | 4/2000 | Tu et al. | 606/41 |

\* cited by examiner

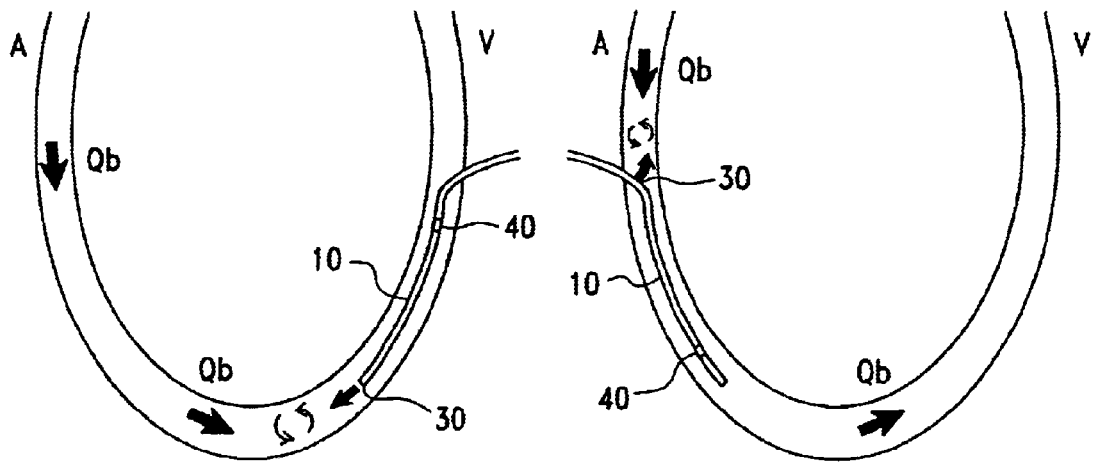
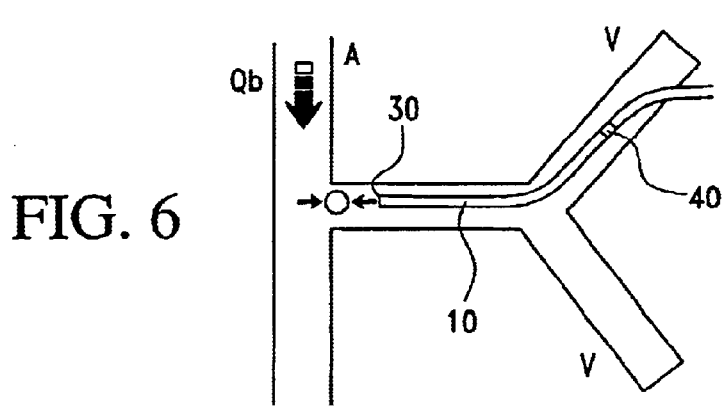
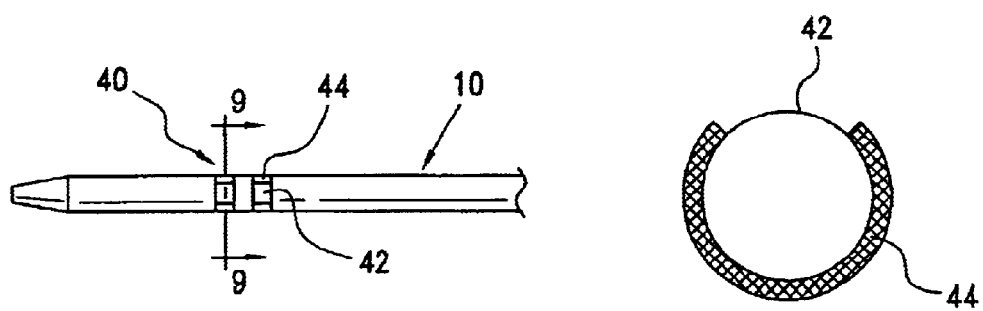

METHOD AND APPARATUS FOR DETERMINING BLOOD FLOW DURING A VASCULAR CORRECTIVE PROCEDURE

FIELD OF THE INVENTION

The present invention relates to blood flow measurements and more particularly, to the real time determination of blood flow during vascular dysfunction corrective procedures whereby the efficacy of the procedures can be determined prior to termination of the session.

BACKGROUND OF THE INVENTION

The use of intravascular catheters for treatment of the body is well known in the field of medicine. The use of dilation or balloon catheters has become widespread in the treatment, for example, of restrictions within the coronary blood vessels, such as stenotic lesions. In balloon angioplasty, a catheter carrying a balloon at its distal end is guided through the blood vessel to a point adjacent the lesion. The placement of the balloon is aided by use of a fluoroscope and radiopaque elements. The size and type of the balloon is generally selected by the physician based on his knowledge of the size and type of lesion. The balloon is then expanded by providing an expansion fluid from the proximal end of the catheter through a fluid lumen within the catheter to the balloon. The expanded balloon acts on the lesion in a manner to reopen at least a portion of the restricted vessel. The balloon is then deflated for removal from the body, though sometimes repeated reinflation may be deemed necessary by the physician prior to removal.

Though balloon angioplasty is well known as a safe and effective method for treatment of the vascular disease described above, there are still problems that arise during the procedure. For example, stenotic lesions often have a highly irregular cross-sectional configuration, and may vary greatly in their hardness, both of which make for difficulty in determining what size and composition of balloon to use, and how often to inflate it. These complications further compound the problem of determining the efficacy of the procedure.

Traditionally, the angioplasty procedure is performed, the catheter is removed and the procedure is terminated. At a later time, days weeks or months, a measurement is taken of blood flow through the previously treated vessel. Depending upon the resulting blood flow, the patient may be again admitted to the facility and another complete angioplasty procedure performed.

Prior methods for determining blood flow through such a reconstructed vessel include injecting a radioactive isotope and monitoring through external equipment passage of the isotope to determine blood flow.

Alternatively, ultrasonic devices have been used to image the vessel prior to reconstruction and re-image the vessel subsequent to reconstruction to obtain two-dimensional images of the vessel. These two-dimensional images are then used as basis for calculating the blood flow through the reconstructed area.

However, each of these procedures is relatively complex in that it involves significant external equipment. In addition, these measurements are taken before and after the entire angioplasty procedure. Thus, if sufficient flow is not restored, the entire angioplasty procedure including reinsertion must be repeated. Thus, the patient is exposed to all the complications of the procedure as well as increased hospital time.

Therefore, need exists for a method and apparatus for determining blood flow during angioplasty procedures such that the efficacy of the procedure and reconstruction of the relevant vessel may be determined in real time. The need continues such that intra-procedural evaluation improvements in access flow may be identified. The need also exists for a relatively simple and inexpensive method and apparatus for determining the intra-procedural blood flow.

SUMMARY OF THE INVENTION

The present invention provides a method and apparatus for the real time determination of access flow during procedures to correct vascular access dysfunction. In particular, the invention provides for the determination of flow by dilution measurement. By determining intra-procedural access flow, the effectiveness of the surgical revision can be promptly assessed and appropriate remedial action promptly taken. As a physician can immediately and accurately determine intervention effectiveness, the procedure may be "tuned" to provide optimal access flow.

The surgical revision may include angioplasty, angioplasty of the arteries and angioplasty of the veins as well as hemodialysis grafts. The access flow may be measured in vascular grafts, arteriovenous shunts, arteriovenous grafts, transcutaneous shunts or fistulas, as well as arteries, veins, vascular ducts and channels, collectively referred to as "vessels".

The present apparatus includes an elongate catheter having an indicator introduction port and a blood property sensor spaced downstream from the port. In addition, it is contemplated the catheter may include a selectively expanding member such as an angioplasty balloon. Thus, the present invention provides an angioplasty catheter with a blood property sensor, wherein the any resulting change in flow rate is determined prior to removal of the catheter.

The present method provides for inserting the angioplasty catheter into a relevant vessel to locate the indicator introduction port upstream of a blood property sensor; locating the sensor to minimize wall effects; forming a first indicator bolus in the bloodstream upstream of the sensor; measuring passage of the first bolus past the sensor; calculating the blood flow in response to the passage of the first indicator bolus, performing the angioplasty procedure; introducing a second indicator bolus through the indicator introduction port; measuring passage of the second indicator bolus past the downstream sensor; and calculating the resulting change in flow. It is understood the vessel may include any vascular passage through which it is desired to measure flow.

As the measurements and calculations are done in real time, an operator is immediately provided an intra-procedural quantitative measurement of flow through the respective vessel in response to the surgical procedure.

In addition, the blood property sensor may be configured to minimize wall effects on the signal from the sensor. That is, the sensor and catheter are configured to maximize sensitivity to the relevant blood property and minimize effects from the local region of the vascular wall. Further, the system is configured to balance the need for a sufficient indicator volume to produce a high quality dilution curve having an acceptable signal-to-noise ratio against an overwhelming of the initial access flow by the introduced indicator. The present system also allows for minimizing the effect indicator introduction on the measured blood volume.

BRIEF DESCRIPTION OF THE DRAWINGS

FIG. 4 is a schematic view of a first configuration of the invention in an operative environment.

FIG. 5 is a schematic view of a second configuration of the invention in an operative environment.

FIG. 6 is a schematic view of an alternative application of the second configuration in an operative environment.

FIG. 8 is a side elevational view of a portion of a catheter showing a blood property sensor.

FIG. 9 is a side elevation view taken along line 9—9 of FIG. 8.

DETAILED DESCRIPTION OF THE PREFERRED EMBODIMENT

Figure 1:
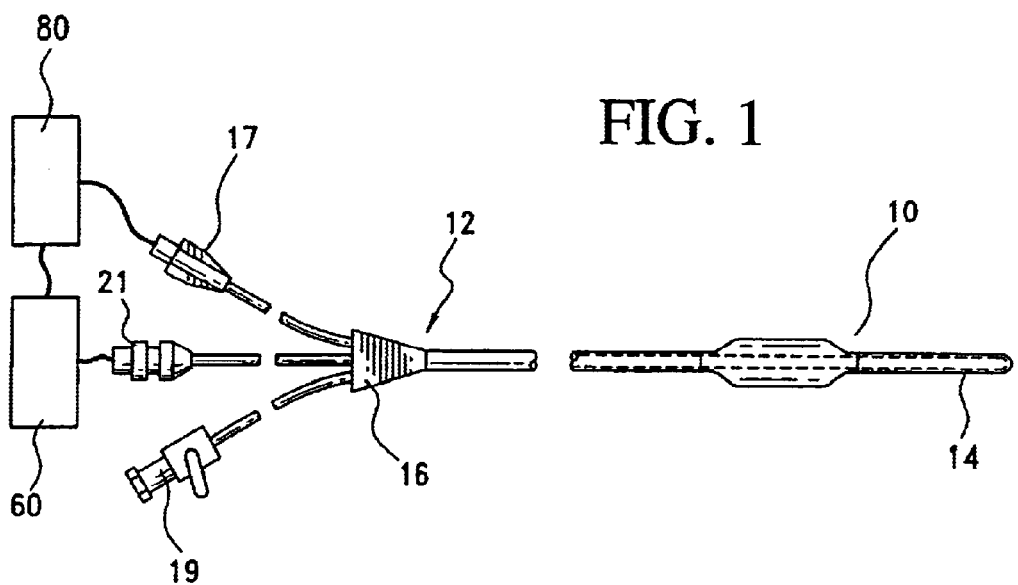
FIG. 1 is a side elevational view of a catheter and an angioplasty expander member.
Figure 2:
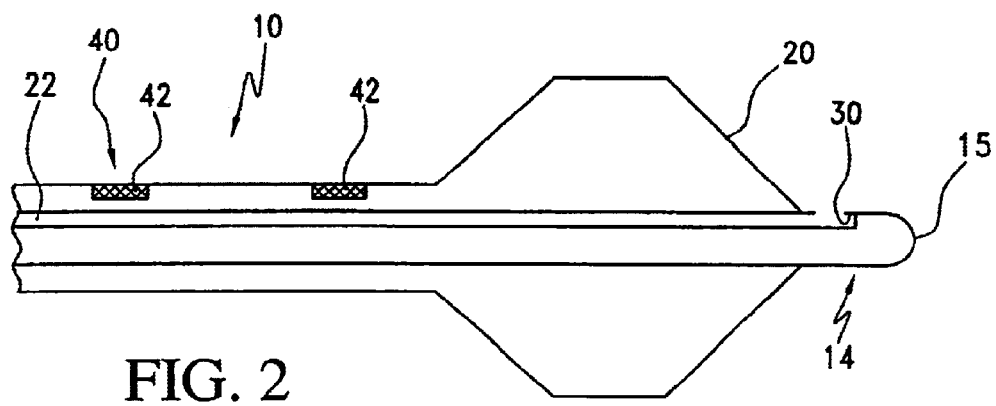
FIG. 2 is a schematic view of a catheter end and angioplasty expander member.
Figure 3:
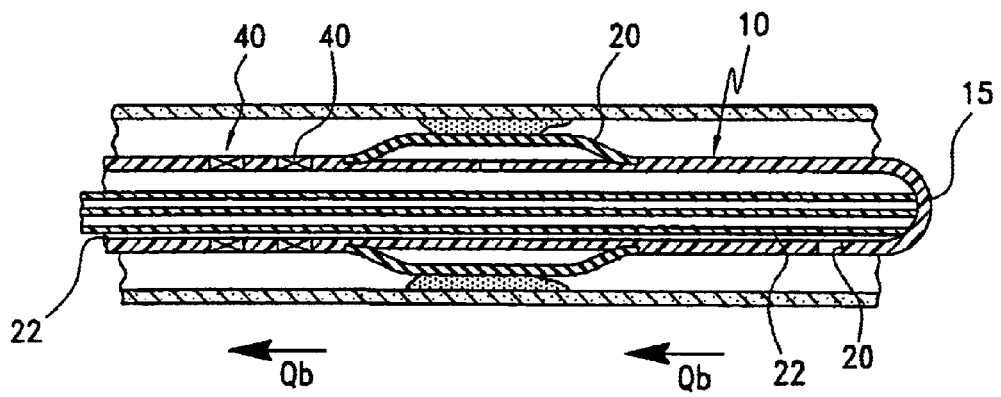
FIG. 3 is an enlarged cross sectional view of the angioplasty expander member in an expanded configuration.

Referring to FIGS. 1–3, the present invention includes an elongate catheter 10 having an indicator introduction port 30 and a spaced apart blood property sensor 40. A controller 60 and a dilution indicator source 80 are selectively connected to the catheter 10.

The present invention provides for intra-procedural measurement of flow through the vascular section in which the catheter is located. Generally, the catheter provides for measurements relating to an inducted change in a blood property. In a preferred configuration, the change in blood property inducted by the introduction of an indicator.

It is understood the indicator is any substance that alters a measurable blood property. The indicator may alter any measurable parameter of the blood. For example, the indicator may be chemical, optical, electrical, thermal or any combination thereof. The particular indicator is at least partly dictated by the anticipated operating environment. Available indicators include saline solutions, increased or decreased temperature as well as dyes and various isotopes. The use of temperature differentials may be accomplished by locally creating a heat source or a heat sink in the surrounding flow. The creation of a local temperature gradient offers the benefit of being able to employ a dilution indicator without introducing any additional volume into the blood flow. That is, a temperature differential may be created without an accompanying introduction of a volume of indicator. Alternatively, a volume of heated or cooled blood may be introduced at the indicator introduction port 30 as the indicator.

Further, the present invention is applicable in a variety of flows including vascular grafts, arteriovenous (AV) shunts, fistula, arterial vessels, venous vessels, arteriovenous grafts, transcutaneous shunts in procedures including hemodialysis and angioplasty.

The present invention may be employed as a dilution catheter and used in conjunction with an angioplasty catheter. Alternatively, the dilution catheter 10 may by incorporated into an angioplasty catheter. As the angioplasty catheter incorporating the indicator introduction port 30 and the spaced apart blood property sensor 40 encompasses the invention, the description will be set forth in terms of the angioplasty catheter.

The present invention is operable in a number of fluid regimes, for purposes of clarity and consistency, the present invention is set forth in a blood flow environment. The term "upstream" of a given position refers to a direction against the flow of blood and the term "downstream" of a given position is the direction the blood flows away from the given position.

FIG. 1 shows the angioplasty catheter 10, the controller 60 and the dilution indicator source 80. The angioplasty catheter 10 has a proximal end 12 and a distal end 14, the distal end ending at a terminus 15. The angioplasty catheter 10 is connected at its proximal end 12 to a manifold 16 and includes an angioplasty expander member 20 at or adjacent the distal end 14. Although the angioplasty expanding member 20 is shown as a balloon, it is understood that any of a variety of devices may be used to reduce a stenosis of a vessel. For example, rotating elements have been employed as well as relatively high pressure fluid streams or sprays, appropriate chemicals, recirculating and non recirculating devices. The present invention may be employed with any of these stenosis reducing devices or techniques, as well as those discussed subsequently in relation to thrombosis.

The angioplasty expander member 20 is selectively expandable to occupy a first contracted cross sectional area and a larger second expanded cross sectional area. The angioplasty expander member 20 may be any of a variety of configurations, and is referred to as a balloon. In contrast to an inflatable member for merely retaining a catheter at a location within a vessel, the present angioplasty expander member is constructed to withstand significantly higher pressures. For example, the present angioplasty balloon can withstand pressures from 5 psi up to 20 psi.

It is understood that locating balloons are used with catheters. These locating balloons are fundamentally different than angioplasty balloons. The locating balloon is an elastic member. Locating balloons are generally spherical and are capable of withstanding just sufficient pressure to partially inflate in the blood flow. Inflation pressures are relatively low, on the order of one psi. The elastic construction of the locating balloon is such that the balloon may be subject to increased inflation pressure and increased diameter up to failure. The geometry of the locating balloon is selected to allow the balloon (and accompanying catheter) to be carried along a vessel by the blood flow. That is, the geometry of the locating balloon sufficiently increases the hydrodynamic resistance to blood flow to translate the balloon and catheter along the vessel.

In contrast, an angioplasty balloon is a generally elongate inelastic inflatable member capable of relatively high pressures. The angioplasty balloon is only expandable to a predetermined size or cross sectional area. Compared to the locating. balloon, angioplasty balloons may require inflation pressures greater than 2 psi and as high as 20 psi or greater. The elongate structure of the angioplasty balloon provides for relatively complete contact along the narrowing of the vessel. That is, the spherical locating balloon presents only a point or ring of contact with the surrounding vessel. The angioplasty balloon contacts a length of the vessel to provide relatively constant pressure along the length of contact. In addition, a slight inflation of the locating balloon is used to increase a resistance to blood flow which in turn causes translation of the balloon along the vessel, thereby allowing the locating balloon to the disposed along a vessel. In contrast, a slight inflation of the angioplasty balloon permits flow around and along the balloon and does not create sufficient resistance to flow to induce translation of the balloon (and catheter) along the vessel. Use of a locating balloon to perform angioplasty would allow an elastic balloon to be inflated within the vessel such inflation of an elastic member could rupture the vessel. Alternatively, the elastic member of the locating balloon may not have sufficient strength to displace the vessel wall and perform the angioplasty.

The manifold 16 includes inlet ports 17, 19 and 21. These inlet ports or additional ports may be adapted to receive desired inputs such as a guide wire to aid in the placement of the balloon within the body vessel. The inlet port 19 may be employed to introduce an inflation fluid through the inlet port to selectively expand the balloon 20.

Referring to FIGS. 2 and 3, inlet port 17 is an indicator inlet for introducing the indicator to the catheter. The angioplasty catheter 10 includes an indicator lumen 22 extending from the indicator inlet 17 in the manifold 16 to the indicator introduction port 30. Preferably, the indicator lumen 22 is located in the interior of the angioplasty catheter 10 and is selectively connected to the indicator source 80. The inlet port 21 is connected to a corresponding lumen for providing communication to the blood property sensor 40. The blood property sensor 40 is operably connected to the controller 60.

The indicator source 80 may be any of a variety of configurations, but is preferably a metered dispenser of the indicator, wherein the volume of indicator and rate of indicator introduction is precisely controlled and measured.

Figure 13:
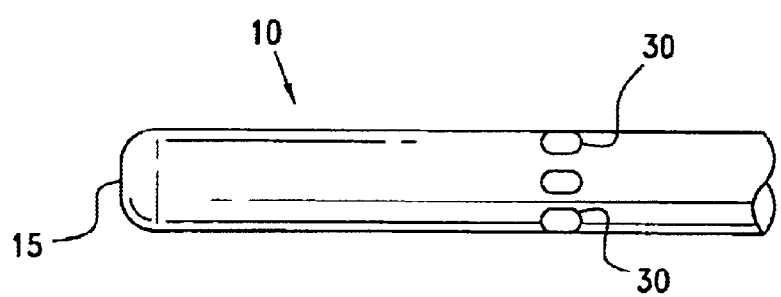
FIG. 13 is a side elevation view of an alternative introduction port configuration.
Figure 14:
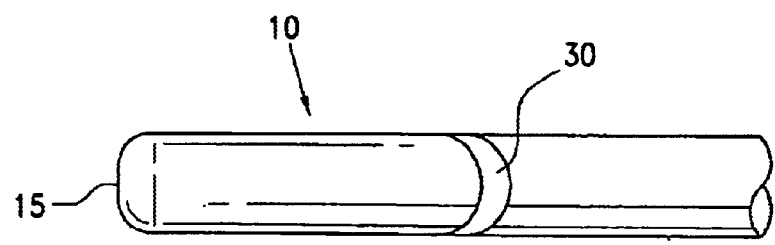
FIG. 14 is a further alternative construction of an indicator introduction port.

It is also contemplated the indicator introduction port 30 may be a local heater or cooler for selectively heating or cooling a blood flow past the indicator introduction port. In this construction, the indicator source 80 is the energy for heating or cooling the flow in the region of the indicator introduction port 30. Referring to FIG. 14, the indicator introduction port 30 may include a heating or cooling element for creating a local temperature gradient in the passing flow. That is, the indicator introduction port 30 encompasses a local heat sink or heat source for creating temperature gradient in the surrounding flow. Thus, a dilution indicator is created without introducing an accompanying volume increase in the flow to be measured. As shown in FIG. 13, the indicator introduction port 30 may include a plurality of radial or axial spaced orifices through which the indicator is introduced into the flow. The particular location and configuration of the orifices are selected to assist in obtaining mixing of the introduced indicator and the blood flow.

Referring to FIG. 3, an over-the-wire balloon angioplasty catheter 10, wherein the angioplasty balloon 20 is shown as sealed to an outer surface of the catheter. It will be recognized that the constructions of the angioplasty balloon as shown in FIG. 3 is merely representative of these elements of the various forms of balloon angioplasty catheters, and that this representative form of drawing has been selected for purposes of clarity in describing the present invention.

As shown in FIGS. 3–6, the blood property sensor 40 is located downstream of the indicator introduction port 30. Thus, depending upon the particular application, the indicator introduction port 30 may be intermediate the distal end 14 of the angioplasty catheter 10 and the sensor 40, or the sensor may be intermediate the distal end of the angioplasty catheter and the indicator introduction port.

Referring to FIGS. 4–6, the blood flow in the vascular passage is identified as Qb, and the arterial side is identified as A and the venous side identified as V.

The sensor 40 is sufficiently spaced from the indicator introduction port 30 to substantially ensure a complete mixing of the introduced indicator with the flow. For artificial grafts, it has been found that a distance greater than approximately 5–6 cm between the indicator introduction port 30 and the downstream sensor 40 is sufficient to ensure mixing. It is understood that local conditions at the point of indicator introduction will effect required distance between the indicator introduction port 30 and the sensor 40. Local conditions include flow rate, turbulence, introduction rate and port configuration. Therefore, the actual distance between the blood property sensor 40 and the indicator introduction port 30 may be determined by number of parameters and the disclosed value may not apply.

The blood property sensor 40 is selected to identify a change in a parameter of the blood. That is, a variation in a blood property is detected by the sensor 40. The particular sensor 40 is at least partially determined by the indicator used. As previously stated, the indicators may be any of a variety of indicator such as, but not limited to impedance, optical, thermal, electrical, density and ultrasound velocity. Thus, depending on the particular indicator, the sensor 40 is accordingly configured. The blood property sensor 40 may be an electrical impedance sensor, an optical sensor, a thermal sensor, sound sensor or even a chemical sensor.

The blood property sensor 40 and the angioplasty catheter 10 are constructed to provide for location of the sensor with respect to the vessel wall so as to minimize wall effects. This is particularly important for electrical impedance sensors. That is, if an electrical impedance sensor is located adjacent to the vessel wall, the impedance measured by the electrical sensor drastically increases thereby jeopardizing an accurate measurement of resistance of the blood flow.

The electrical impedance sensor records a change in the electrical impedance of the blood induced by the introduced indicator. However, it has been found that a narrow vascular passage that locates an electrical sensor adjacent the wall can render improper readings. Specifically, impedance drastically increases upon locating the sensor in contact with the vascular wall. Thus, a configuration of the present invention includes a sensor 40 constructed to maximize sensitivity to blood electrical impedance and minimize sensitivity to the vessel wall.

In one configuration as shown in FIGS. 8 and 9, the electrical impedance sensor 40 includes a pair of spaced apart conductive rings 42 on the catheter 10. Each ring 42 includes a non conducting portion or break 44. The non conducting portion 44 may alternatively be formed by disposing an insulating layer on a portion of the ring 42. The insulating layer may be a biologically appropriate paint. The non conducting portion 44 is used in locating the catheter with respect to the vascular wall. The sensor 40 is constructed so that the electrical field will preferentially propagate in the blood. The rings 42 are sufficiently close to each other so that the electrical field is confined to a relatively small volume between the rings.

In an alternative configuration to minimize wall effects, a plurality of spaced sensor may be located about a circumference of the catheter 10. In this configuration, the conductive portion of the ring is again designated as 42 and the non conductive portion is set forth as 44. In this construction, each conductive area is operably connected to the controller 60.

Preferably, the conductive rings 42 are formed of stainless steel. The distance between the conductive rings 42 is selected (1) to be sufficiently small to concentrate the electrical filed between the electrodes to minimize the influence of the vascular wall, and (2) large enough to eliminate the negative electrode effects (i.e. polarization) of highly concentrated electrical fields in a bipolar system.

Thus, the electrical impedance sensors may be located to occupy only a specific portion of the angioplasty catheter periphery. Preferably, the electrical sensors are longitudinally spaced (separated) and occupy a common longitudinal section of the periphery.

More generally, it is understood that controlled catheter rotation may be employed to determine the best position of the sensor with respect to the vessel wall as well as the screening of signals from multiple sensors to identify the most appropriately located sensors. In addition, the sensors may be any of a variety of blood property sensors including optical, thermal and any other chemical or physical property.

Alternatively, the angioplasty catheter 10, or a local section of the catheter may be formed of a sufficiently rigid material so that a slight bend or curvature may be formed and retained in a length of the catheter to form a concave section. The sensor 40 is then located within the concave section and is shielded by the concavity so as to be displaced from the adjacent vessel wall.

More generally, an outer wall of the angioplasty catheter 10 may include a recess sized to receive the sensor 40. Upon locating the sensor 40 within the recess wall effects may be substantially precluded.

The controller 60 is operably connected to the sensor 40 and the indicator source 80. The controller 60 includes a processor for performing the calculations necessary to provide the flow rate.

The controller 60 may be configured to provide the necessary electrical signal to the electrical impedance sensor. An anticipated frequency will be approximately 100 kHz.

Figure 7:
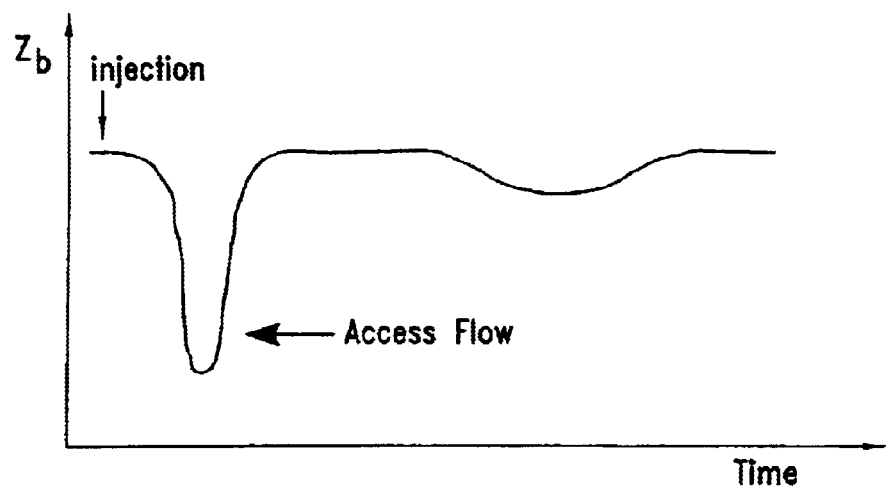
FIG. 7 is a graph representing passage of the indicator bolus past the sensor.

For example in measuring hemodialysis vascular access flow, the controller 60 measures the access flow by monitoring the passage of completely mixed indicator in the blood. Referring to FIG. 7, the concentration curve resulting from the introduction and mixing of the indicator is recorded by the sensor. Access flow, AF, is then calculated according to:

$$AF = \frac{V}{\int C(t)dt}$$

where V is the volume of indicator introduced, $\int C(t)dt$ is the area under the dilution curve that is equal to the average concentration of the indicator in the flow for the duration of the curve multiplied by the duration of the dilution curve.

To provide accuracy of the measurement, as shown in FIGS. 4–6, the indicator should by completely mixed with the flow and effects resulting from the proximity of the vascular wall and the sensor should be minimized.

For the electrical impedance dilution sensor, the access flow, AF, can be calculated according to:

$$AF = V \frac{2Zb}{\int \Delta Zb(t)dt}\left[1 + \sqrt{\frac{Zb}{Zi}}\right]$$

where Zb is the electrical impedance of the blood and Zi is the electrical impedance of the indicator (in ohms); and $\Delta Zb(t)$ is the change in electrical impedance from a baseline at time t due to the injection of the indicator.

Figure 11:
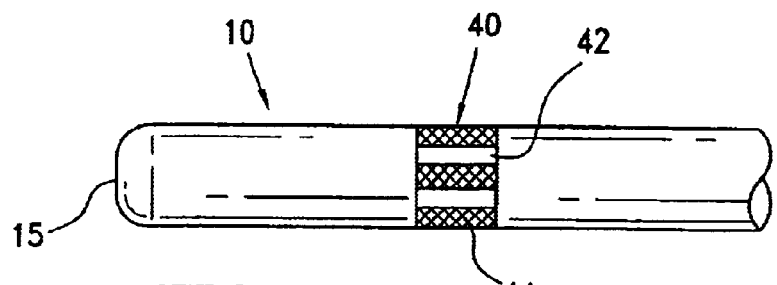
FIG. 11 is a side elevational view of an alternative sensor configuration.

More specifically, the access flow for a bolus injection, as shown in FIG. 11, may be calculated from:

$$AF \cong V\frac{Z_b}{\int \Delta Z_b(t)_{S\%}dt}(S\% + 0.51)\left(1 + \frac{0.27Z_b}{S\% \times Z_s}\right)$$

where V is the volume of the saline bolus [ml], $Z_b$ is the blood electrical impedance measured in ohms, $Z_s$ is the saline electrical impedance measured in ohms, S% is the concentration of saline, $\Delta Z_b(t)$ is the change in the electrical impedance from a baseline at time t due to injection of the indicator in ohms, $\int \Delta Z_b(t)_{S\%}dt$ is the area under the blood electrical impedance dilution curve [ohm×min.].

Figure 12:
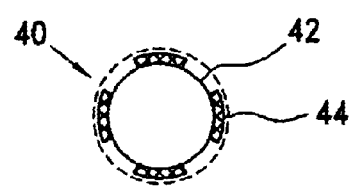
FIG. 12 is a cross sectional view taken along line 12—12 of FIG. 11.

Similarly, the access flow for a constant infusion, as shown in FIG. 12, may be determined from:

$$AF \cong Q_{S\%}\frac{Z_b}{\Delta Z_b(t)_{S\%}}(S\% + 0.51)\left(1 + \frac{0.27Z_b}{S\% \times Z_s}\right)$$

where $Q_{s\%}$ is the infusion speed of the saline [ml/min], $Z_b$ is the blood electrical impedance measured in ohms, $Z_s$ is the saline electrical impedance measured in ohms, S% is the concentration of saline, and $\Delta Z_b(t)_{s\%}$ is the blood electrical impedance baseline shift corresponding to the saline infusion.

The controller 60 may be further configured to determine an effective cross sectional area of the vascular access. Effective cross sectional area directly effects the hydrodynamic resistance of the vascular access and may be useful as an additional independent criteria of vascular access condition.

As the controller 60 is connected to or receives the time, t, of indicator injection by the indicator source 80 and the sensor provides a signal corresponding to passage of the indicator, the transit time of the indicator between the indicator introduction port 30 and the sensor 40 is provided to the controller. The controller 60 multiplies the transit time by the calculated access flow to determine the volume between the indicator injection port 30 and the sensor 40. That is, the flow rate equals the cross sectional area multiplied by the flow velocity. Thus, the effective cross sectional area S may be calculated from:

$$S = AF\left(\frac{MTT}{L}\right);$$

where MTT is the mean transit time of the indicator passing the distance L from the indicator injection port 30 to the sensor 40.

Operation

In operation, the angioplasty catheter 10 may be employed in either of two configurations, (i) where the distal end 14 of the angioplasty catheter is the upstream portion of the angioplasty catheter as shown in FIG. 4, or (ii) where the distal portion of the angioplasty catheter is the downstream end, as shown in FIG. 5. In either configuration, the angioplasty catheter 10 is inserted into the vessel to locate the indicator introduction port 30 upstream of the sensor 40.

An indicator is introduced through the indicator introduction port 30 from the indicator source 80. It is understood that if a thermal indicator were employed, the localized heating or cooling of the blood flow would not result in any introduction of indicator, but would be an indicator formation. The indicator is thus formed or introduced upstream of the sensor 40.

As at least partially determined by the environment, the sensor 40 is located a sufficient distance downstream of the indicator introduction port 30 to ensure mixing of the indicator with the blood flow.

Figure 10:
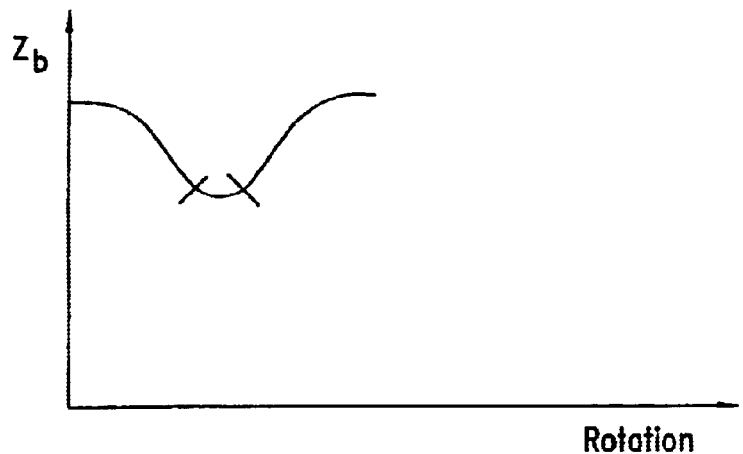
FIG. 10 is a graph representing measured electrical impedance in relation to rotation of the sensor of FIGS. 8 and 9 adjacent a vascular wall.
Figure 15:
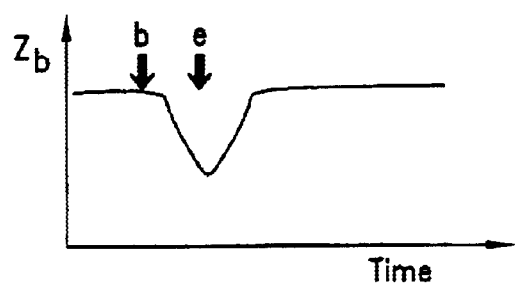
FIG. 15 is a graph representing passage of an electrical impedance indicator bolus.
Figure 16:
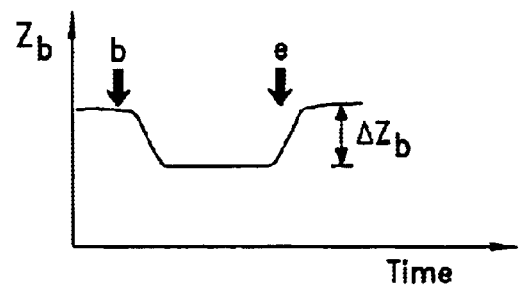
FIG. 16 is a graph representing a constant infusion of an electrical impedance indicator.

The sensor 40 is located to minimize the wall effects. As shown in FIG. 10 by rotating the catheter, the rings 42 are moved relative to the adjacent vascular wall. By rotating the sensor 40 to locate the orientation of minimal impedance, as shown between the lines on the graph, the sensor is located to measure the electrical impedance from the blood flow, rather than the adjacent wall. Thus, the catheter 10 is rotated to locate the sensor 40 so that the impedance is minimal.

If the configuration of the electrical sensor having a plurality of circumferentially spaced conductive areas is employed, the resulting impedance measurement is monitored for each area and those areas having adverse wall effects are not employed by the controller 60, while those areas having a minimized wall effect are relied upon by the controller 60.

Alternatively, the controller 60 will simultaneously employ the signals of all sensors using an algorithm to optimize the results with best elimination of wall effects. Alternatively, the plurality of sensors may be read by the controller in a sequential manner and the appropriate sensor (s) employed.

The blood flow causes the indicator bolus to pass the downstream sensor 40. Passage of the bolus is measured by the sensor 40. The blood flow may then be calculated by the controller 60.

The angioplasty procedure is then performed. That is, the angioplasty balloon is inflated and the vessel is locally expanded. It is understood the procedure may be any of the previously recited operations.

A subsequent blood flow measurement is then taken again by introducing a second indicator bolus (or forming a second indicator bolus) upstream of the sensor 40, and measuring passage of the bolus past the sensor and calculating the flow rate.

The operator may thus readily identify any increase in blood flow through the vessel and repeat the procedure as necessary.

It is understood that some procedures, such as vascular access in hemodialysis, there may be sufficient vessel volume to accommodate two catheters. In such situations it is anticipated an angioplasty catheter and a separate dilution sensor catheter may be employed. That is, the expander balloon 20 is located on a separate catheter from the sensor 40. In this operating configuration, the present system again allows for intra-procedural measurement of the flow by employing the dilution techniques set forth herein, for flow measurement before, during and after the angioplasty procedure.

It is also considered that the present invention may be employed subsequent to an angioplasty procedure. That is, in using either the combined angioplasty-sensor catheter or separate angioplasty catheter and sensor catheter, the angioplasty procedure may be performed and then the blow flow determined. Although no prior measurement is made with device, an after angioplasty measurement can be made. The after angioplasty measurement may be compared to a base line value, if desired.

It is understood, the present invention is applicable to corrective procedures for thombosed or malfunctioning vascular access as well as occluded or partially occluded vessels, including but not limited to, stenosed ducts, channels, canals, tubes, vessels or the like. The term stenosis is taken to encompass all these terms as well as any narrowing or reduction of a passage through which flow is to be restored. The use of the present invention in connection with the procedure provides the real time evaluation of the procedure.

The corrective procedures include, but are not limited to, the removal of a thrombus, angioplasty, atherectomy or dislodgment of a thrombus. The removal of a thrombus may be accomplished in a variety of ways including (i) pharmacomechanical thrombolysis using urokimas; (ii) pulse-spray thrombolysis using herparinized saline; (iii) balloon thrombectomy techniques; and (iv) mechanical thrombectomy devices, including recirculation type devices and non-recirculation type devices.

In addition, the flow calculation may be performed prior to the corrective procedure, after the corrective procedure or before and after the corrective procedure, to provide intra-procedural flow measurements.

Thus, the present invention provides intra-operative evaluation of access flow during surgical procedure to allow more rapid restoration of a more functional graft, extend access life and reduce the incidence and expense of full access revision surgery. The immediate feedback of access flow, including arterial and venous flow, in response to the angioplasty permits the operator to maximize the effect of the procedure as well as reduce the need for repeating the procedure.

While the invention has been described with reference to preferred embodiments, it will be understood by those skilled in the art that various changes may be made and equivalents may be substituted for elements thereof without departing from the scope of the invention. In addition, many modifications may be made to adapt a particular situation of material to the teachings of the invention without departing from the scope of the invention. Therefore, it is intended that the invention not be limited to the particular embodiments disclosed as the best mode contemplated for carrying out this invention, but that the invention will include all embodiments falling within the scope and spirit of the appended claims.

What is claimed:

1. A method for quantitatively measuring a reduced stenosis induced flow change, comprising:

(a) inserting a catheter and a blood property sensor into a vessel having a brood flow corresponding to the stenosis;

(b) introducing from an indicator source a first change in a blood property in a blood flow outside the catheter at a fixed distance from the blood property sensor and upstream of the blood property sensor;

(c) detecting passage of the first change in the blood property at the blood property sensor;

(d) reducing the stenosis in the vessel;

(e) introducing from the indicator source a second change in the blood property upstream of the sensor;

(f) detecting passage of the second change in the blood property at the blood property sensor; and (g) determining at a controller connected to the indicator source and the sensor a change in blood flow corresponding to (i) the detected passage of the first change in the blood property and (ii) the second change in the blood property.

2. The method of claim 1, wherein inserting a catheter and a blood property sensor into a vessel includes inserting a first catheter having a stenosis reducing member and a second catheter having the blood property sensor, the first catheter and the second catheter being connected to locate the blood property sensor at a fixed location relative to the stenosis reducing member.

3. The method of claim 1, wherein inserting a catheter and a blood property sensor into a vessel includes inserting a catheter having a stenosis reducing member and the blood property sensor.

4. The method of claim 1, wherein introducing the first change in the blood property includes introducing one of a bolus injection and a constant infusion.

5. The method of claim 1, wherein introducing the second change in the blood property includes introducing one of a bolus injection and a constant infusion.

6. A method of monitoring blood flow during a vascular corrective procedure, comprising:
 (a) inserting a catheter into a vessel;
 (b) employing the catheter to perform a vascular correction in the vessel;
 (c) introducing from an indicator source a first blood property change into a blood flow outside the catheter;
 (d) detecting passage of the first blood property change past a downstream sensor on the catheter; and
 (e) calculating the blood flow at a controller operably connected to the indicator source and the downstream sensor in response to the change in blood property and passage of the blood property past the downstream sensor.

7. The method of claim 6, wherein introducing the first blood property change includes introducing one of a bolus injection and a constant infusion.

8. A method of monitoring a stenosis reducing procedure in a vessel, comprising:
 (a) locating a blood parameter altering section connected to a rate and volume measured indicator source in the vessel to alter a blood parameter in a blood flow contacting the vessel;
 (b) locating a blood parameter sensor a fixed distance downstream of the altering section;
 (c) performing the stenosis reducing procedure; and
 (d) determining in a controller connected to the indicator source and the blood parameter sensor a blood flow in response to a passage of an altered blood property past the blood parameter sensor.

9. The method of claim 8, wherein performing the stenosis reducing procedure includes angioplasty.

10. The method of claim 8, further comprising locating the blood parameter sensor to reduce wall effects from the vessel.

11. The method of claim 8, further comprising rotating the blood parameter sensor with respect to the vessel to reduce wall effects from the vessel.

12. The method of claim 8, further comprising locating a plurality of blood parameter sensors in the vessel.

13. The method of claim 8, further comprising altering the blood property by introducing one of a bolus injection and a constant infusion.

* * * * *